(12) United States Patent
Hwang

(10) Patent No.: US 7,091,029 B2
(45) Date of Patent: Aug. 15, 2006

(54) HIGH TITER RECOMBINANT AAV PRODUCTION

(75) Inventor: Kyu-Kye Hwang, Gainsville, FL (US)

(73) Assignee: Applied Genetics Technologies Corporation, Alachua, FL (US)

( * ) Notice: Subject to any disclaimer, the term of this patent is extended or adjusted under 35 U.S.C. 154(b) by 0 days.

(21) Appl. No.: 10/252,182

(22) Filed: Sep. 23, 2002

(65) Prior Publication Data

US 2004/0058439 A1 Mar. 25, 2004

(51) Int. Cl.
| | |
|---|---|
| C12N 7/00 | (2006.01) |
| C12N 7/02 | (2006.01) |
| C12N 15/86 | (2006.01) |
| C12P 21/06 | (2006.01) |
| A01N 63/00 | (2006.01) |
| C07H 21/02 | (2006.01) |

(52) U.S. Cl. .................. 435/235.1; 435/239; 435/456; 435/320.1; 435/69.1; 424/93.2; 536/23.1; 536/24.1

(58) Field of Classification Search ............. 435/235.1, 435/239, 456, 320.1, 69.1; 424/93.2; 536/23.1, 536/24.1
See application file for complete search history.

(56) References Cited

U.S. PATENT DOCUMENTS

| | | | |
|---|---|---|---|
| 5,965,441 A | 10/1999 | Breakefield et al. | |
| 6,383,794 B1 * | 5/2002 | Mountz et al. ........... | 435/235.1 |
| 6,596,269 B1 * | 7/2003 | Iadarola et al. ............ | 424/93.2 |
| 6,686,200 B1 * | 2/2004 | Dong et al. ................. | 435/457 |
| 2002/0051769 A1 * | 5/2002 | Zhang ..................... | 424/93.21 |
| 2002/0058341 A1 * | 5/2002 | Nakai et al. ................ | 435/456 |

OTHER PUBLICATIONS

Knipe, D. "The Role of Viral and Cellular Nuclear Proteins in Herpes Simplex Virus Replication," Advances in Virus Research, vol. 37: 85-123, 1989.
Clark, K. "Recent Advances in Recombinant Adeno-Associated Virus Vector Production," Kidney International, vol. 61, Symposium 1 (2002): S9-S15, 2002.
Rutledge, et al., "Infectious Clones and Vectors Derived From Adeno-Associated Virus (AAV) Serotypes Other Than AAV Type 2," Journal of Virology, vol. 72: 309-319, 1998.
Xiao, et al., "Gene Therapy Vectors Based on Adeno-Associated Virus Type 1," Journal of Virology, vol. 73: 3994-4003, 1999.
Chiorini, et al., "Cloning and Characterization of Adeno-Associated Virus Type 5," Journal of Virology, vol. 73: 1309-1319, 1999.
Chiorini, et al., "Cloning of Adeno-Associated Virus Type 4 (AAV4) and Generation of Recombinant AAV4 Particles," Journal of Virology, vol. 71: 6823-6833, 1997.
Xiao, et al., "Production of High-Titer Recombinant Adeno-Associated Virus Vectors in the Absence of Helper Adenovirus," Journal of Virology, vol. 72: 2224-2232, 1998.
Herzog, et al., "Stable Gene Transfer and Expression of Human Blood Coagulation Factor IX After Intramuscular Injection of Recombinant Adeno-Associated Virus," Proc. Natl. Acad. Sci. USA, vol. 94: 5804-5809, 1997.
Hermonat, et al., "Use of Adeno-Associated Virus as a Mammalian DNA Cloning Vector: Transduction of Neomycin Resistance into Mammalian Tissue Culture Cells," Proc. Natl. Acad. Sci. USA, vol. 81: 6466-6470, 1984.
Conway, et al., "Recombinant Adeno-Associated Virus Type 2 Replication and Packaging Is Entirely Supported by a Herpes Simplex Virus Type 1 Amplicon Expressing Rep and Cap," Journal of Virology, vol. 71: 8780-8789, 1997.
Zolotukhin, et al., "Recombinant Adeno-Associated Virus Purification Using Novel Methods Improves Infectious Titer and Yield," Gene Therapy, vol. 6: 973-985, 1999.
Halbert, et al., "Transduction by Adeno-Associated Virus Vectors in the Rabbit Airway: Efficiency, Persistence, and Readministration," Journal of Virology, vol. 71: 5932-5941, 1997.
Conway, et al., "High-Titer Recombinant Adeno-Associated Virus Production Utilizing a Recombinant Herpes Simplex Virus Type I Vector Expressing AAV-2 Rep and Cap," Gene Therapy, vol. 6: 986-993, 1999.
Monahan, et al., "Direct Intramuscular Injection With Recombinant AAV Vectors Results in Sustained Expression in a Dog Model of Hemophilia," Gene Therapy, vol. 5: 40-49, 1998.
Matsushita, et al., "Adeno-Associated Virus Vectors can be Efficiently Produced Without Helper Virus," Gene Therapy vol. 5: 938-945, 1998.
Koeberl, et al., "Persistent Expression of Human Clotting Factor IX From Mouse Liver After Intravenous Injection of Adeno-Associated Virus Vectors," Proc. Natl. Acad. Sci. USA, vol. 94: 1426-1431, 1997.
Kessler, et al., "Gene Delivery to Skeletal Muscle Results in Sustained Expression and Systemic Delivery of a Therapeutic Protein," Proc. Natl. Acad. Sci. USA, vol. 93: 14082-14087, 1996.

(Continued)

Primary Examiner—Dave Trong Nguyen
Assistant Examiner—Maria Marvich
(74) Attorney, Agent, or Firm—Peter F. Corless, Esq.; Margaret J. McLaren, Esq.; Edwards Angell Palmer & Dodge LLP

(57) ABSTRACT

The invention includes methods and compositions for the production of high titer recombinant adeno-associated virus (rAAV). The disclosed rAAV are useful in gene therapy applications. Methods are based on the use of recombinant herpes virus vectors and result in highly efficient production of rAAV.

26 Claims, 7 Drawing Sheets

OTHER PUBLICATIONS

Figure 1:
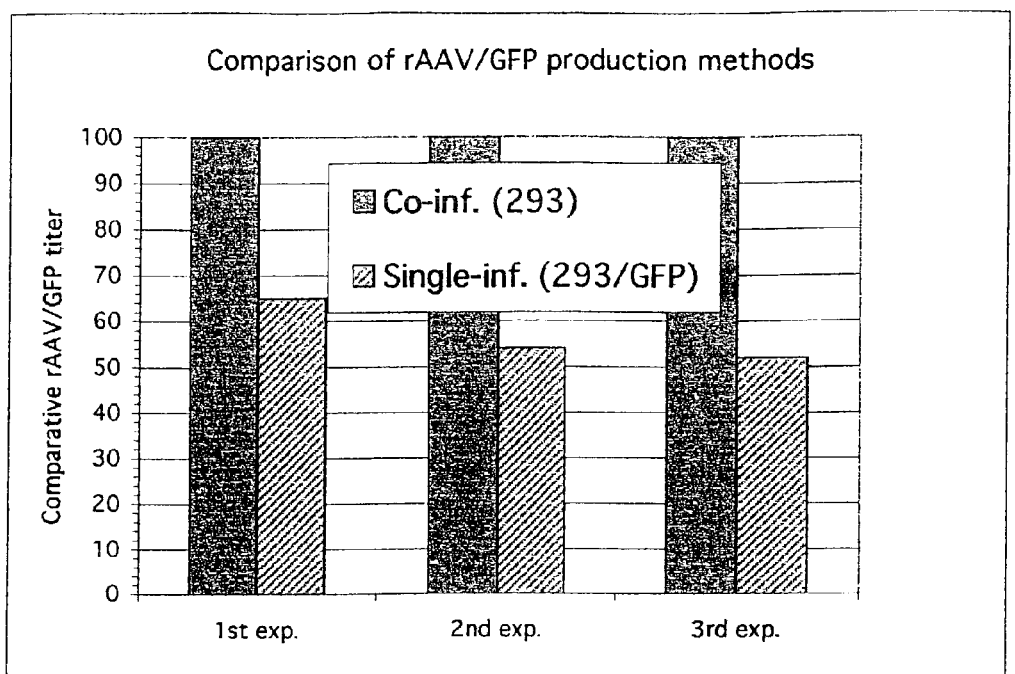

Nakai, et al., "Adeno-Associated Viral Vector-Mediated Gene Transfer of Human Blood Coagulation Factor IX into Mouse Liver," Blood, vol. 91: 4600-4607, 1998.

Clark, et al., "Cell Lines for the Production of Recombinant Adeno-Associated Virus," Human Gene Therapy vol. 6: 1329-1341, 1995.

Gao, et al., "High-Titer Adeno-Associated Viral Vectors From a Rep/Cap Cell Line and Hybrid Shuttle Virus," Human Gene Therapy vol. 9: 2353-2362, 1998.

Johnston, et al., "HSV/AAV Hybrid Amplicon Vectors Extend Transgene Expression in Human Glioma Cells," Human Gene Therapy vol. 8: 359-370, 1997.

Buller, et al., "Herpes Simplex Virus Types 1 and 2 Completely Help Adenovirus-Associated Virus Replication," Journal of Virology, vol. 40: 241-247, 1981.

McCarthy, et al., "Herpes Simplex Virus Type 1 ICP27 Deletion Mutants Exhibit Altered Patterns of Transcription and are DNA Deficient," Journal of Virology, vol. 63, 18-27, 1989.

Samulski, et al., "Rescue of Adeno-Associated Virus From Recombinant Plasmids: Gene Correction Within the Terminal Repeats of AAV," Cell, vol. 33: 135-143, 1983.

Kaplitt, et al., "Long-Term Gene Expression and Phenotypic Correction Using Adeno-Associated Virus Vectors in the Mammalian Brain," Nature Genetics, vol. 8: 148-154, 1994.

Sandri-Goldin, et al., "A Herpesvirus Regulatory Protein Appears to Act Post-Transcriptionally by Affecting mRNA Processing," Genes & Development, vol. 6: 848-863, 1992.

Wagner, et al., "Efficient and Persistent Gene Transfer of AAV-CFTR in Maxillary Sinus," The Lancet, vol. 351: 1702-1703, 1998.

Rice, et al., "Genetic Evidence for Two Distinct Transactivation Functions of the Herpes Simplex Virus α Protein ICP27," Journal of Virology, vol. 64, 1704-1715, 1990.

Weindler, et al., "A Subset of Herpes Simplex Virus Replication Genes Provides Helper Functions for Productive Adeno-Associated Virus Replication," Journal of Virology, vol. 65, 2476-2483, 1991.

Ye, et al., "Regulated Delivery of Therapeutic Proteins After in Vivo Somatic Cell Gene Transfer," Science, vol. 283: 88-91, 1999.

Rose, et al., "Adenovirus-Associated Virus Multiplication VII. Helper Requirement for Viral Deoxyribonucleic Acid and Ribonucleic Acid Synthesis," Journal of Virology, vol. 10: 1-8, 1972.

Snyder, et al., "Efficient and Stable Adeno-Associated Virus-Mediated Transduction in the Skeletal Muscle of Adult Immunocompetent Mice," Human Gene Therapy, vol. 8: 1891-1900, 1997.

Hauswirth, et al., "Production and Purification of Recombinant Adeno-Associated Virus," Methods In Enzymology, vol. 316: 743-761, 2000.

Flotte, et al., "Adeno-Associated Virus Vectors for Gene Therapy of Cystic Fibrosis," Methods In Enzymology, vol. 292: 717-732, 1998.

Muzyczka, et al., "Parvoviridae: The Viruses and Their Replication," Fields Virology, Fourth Edition, 2327-2359, 2001.

Muzyczka, N., "Use of Adeno-Associated Virus as a General Transduction Vector for Mammalian Cells," Curr. Top Microbiol. Immunol., 158: 97-129, 1992.

* cited by examiner

HIGH TITER RECOMBINANT AAV PRODUCTION

1.0 BACKGROUND OF THE INVENTION

1.1 Field of The Invention

The invention is in the field of molecular biology. More specifically, the invention relates to methods for the large-scale production of recombinant adeno-associated virus (rAAV) for use in gene therapy applications.

1.2 Description of The Related Art

Gene therapy refers to treatment of genetic diseases by replacing, altering, or supplementing a gene responsible for the disease. It is achieved by introduction of a corrective gene or genes into a host cell, generally by means of a vehicle or vector. Gene therapy holds great promise for the treatment of many diseases. Already, some success has been achieved pre-clinically, using recombinant AAV (rAAV) for the delivery and long-term expression of introduced genes into cells in animals, including clinically important non-dividing cells of the brain, liver, skeletal muscle and lung. Clinical trials using this technology have included use of rAAV expressing the cftr gene as a treatment for cystic fibrosis (Flotte et al., 1998; Wagner et al. 1998).

Methods for production of rAAV have been developed in which cells grown in culture are caused to produce rAAV, which is harvested from the cells and purified. Production methods for rAAV involve delivery of three necessary elements to the producer cells: 1) a gene of interest flanked by AAV ITR sequences, 2) AAV rep and cap genes, and 3) helper virus proteins ("helper functions"). The conventional protocol for delivering the first two is by transfection of the cells with plasmid DNA containing the appropriate recombinant gene cassettes The helper functions have traditionally been supplied by infecting the cells with a helper virus such as adenovirus (Ad). (Samulski et al., 1998; Hauswirth et al., 2000).

1.3 Quantitative Problems Associated With Producing Amounts of rAAV Needed for Gene Therapy Despite the potential benefits of gene therapy as a treatment for human genetic diseases, unfortunately, a serious practical limitation stands in the way of its widespread use in the clinic. In order to produce even a single clinically effective dose for a human patient, over $10^{14}$ rAAV particles must be made (Snyder, et al., 1997; Ye et al., 1999). To make this number of particles using current technology requires over $2 \times 10^{11}$ producer cells. On a laboratory scale, this number of cells would require about 7500 tissue culture flasks. On a commercial scale, this level of cell culture poses a serious practical barrier to large scale production of rAAV in "cell factories."

The benefits of improving particle yield per cell will be very significant from a commercial production standpoint. For example, an improvement resulting in a two-fold increase in rAAV yield per cell would allow for culture of half as many cells. A ten-fold increase would enable the same amount of rAAV product to be made by one-tenth the number of producer cells. Significant improvements of this magnitude are required in order to achieve economic feasibility for this technology.

Current rAAV production methodologies make use of procedures known to limit the number of rAAV that a single producer cell can make. The first of these is transfection using plasmids for delivery of DNA to the cells. It is well known that plasmid transfection is an inherently inefficient process requiring high genome copies and therefore large amounts of DNA (Hauswirth et al., 2000). Additionally, use of Ad significantly reduces the final rAAV titers because it is a contaminant that must be removed from the final product. Not only must effective procedures be employed to eliminate Ad contamination, but stringent assays for Ad contamination of rAAV are also necessary. Purification and safety procedures dictated by the use of Ad result in loss of rAAV at each step. To overcome the major barrier to the routine use of gene therapy, commercially practical methods must be developed to provide rAAV in the vast amounts required for clinical applications.

2.0 SUMMARY OF THE INVENTION

The present invention seeks to overcome some of the deficiencies in the prior art by addressing problems that limit production of rAAV in sufficient quantities for efficient gene therapy procedures. In the invention, high titers of infectious rAAV are obtained that are at least an order of magnitude greater than previously reported.

The invention is a novel method for producing high titer rAAV. In the method, producer cells are simultaneously co-infected with at least two recombinant herpes simplex viruses (rHSV). The two rHSV are vectors designed to provide the cells, upon infection, with all of the components necessary to produce rAAV. The method does not require the use of producer cells specialized for expression of particular gene products. This is advantageous because the invention can be practiced using any producer cell generally suitable for this purpose. Examples of suitable producer cells include but are not limited to cell lines such as 293, 293-GFP, Vero, V27 and C12 cells.

Any rHSV suitable for the purpose can be used in the invention. Embodiments of the rHSV used in the invention can be replication defective. Infection of producer cells with rHSV that is incapable of replication is preferred because in contrast to methods involving use of adenovirus, the rHSV does not become a significant contaminant of the rAAV product. This increases the final yield of rAAV by eliminating purification steps associated with removal of Ad. In a particular embodiment of the invention, the rHSV was constructed from a mutant of HSV-1 in which the inability to replicate is due to a mutation in the ICP27 gene. Any other suitable mutants of HSV exhibiting a replication-defective phenotype can also be used to construct the rHSV.

In one embodiment, the first rHSV vector contains the AAV rep and cap genes. Other rHSV vectors can be used, such as rHSV containing either rep or cap genes. Embodiments of the first rHSV of the method include but are not limited to gene constructs based on variants of the cap gene found in various serotypes of AAV including AAV-1, AAV-2, AAV-3, AAV-4, AAV-5 and AAV-6, AAV-7 and AAV-8. Also within the scope of the invention are novel AAV serotypes, and those modified by recombination or mutation of existing serotypes.

In certain embodiments, the AAV-2 rep and cap genes in the first rHSV may be driven by their native promoters, and the gene construct is inserted into the tk gene of rHSV virus. One may also utilize any other site or sites in the HSV genome suitable for integration of the rep and cap genes. Additionally, heterologous promoters may be used to drive expression of the AAV genes. Examples of other promoters that can be used in the disclosed method include but are not limited to the SV40 early promoter, CMV promoter, Herpes tk promoter, metallothionine inducible promoter, mouse mammary tumor virus promoter and chicken β-actin promoter.

The second rHSV contains inverted terminal repeats (ITRs) from AAV with one or more genes of interest driven by one or more promoters. In some embodiments, the gene of interest is inserted between a pair of ITRs. The gene of interest may be a gene likely to be of therapeutic value. Examples of therapeutic genes include but are not limited to α-1 antitrypsin, GAA, erythropoietin and PEDF. When it is desirable to select for or to identify successful transgene expression, the gene of interest may be a reporter gene. Many examples of genes used as reporters or for selection are known, and can be used in the invention. These include but are not limited to, the genes encoding beta-galactosidase, neomycin, phosphoro-transferase, chloramphenicol acetyl transferase, thymidine kinase, luciferase, beta-glucuronidase, aminoglycoside, phosphotransferase, hygromycin B, xanthine-guanine phosphoribosyl, luciferase, DHFR/methotrexate, and green fluorescent protein (GFP).

The invention provides a method of producing high titer rAAV in which the yield of rAAV is in the range of at least up to 5000–6000 infectious particles per producer cell. In developing the novel rHSV-based, Ad-free system for rAAV production, factors were discovered that greatly affected the yield of infectious rAAV per cell. Highly significant among these was the use of simultaneous co-infection of the producer cells with two different rHSVs. Serial infection was at best about 35% as effective as simultaneous co-infection, and at worst resulted in negligible production of rAAV. Other factors affecting yields include the relative proportions of the first and second rHSV, the duration of incubation times following simultaneous co-infection, choice of producer cells, culture conditions for producer cells, and cells used for titration of rAAV stocks.

The invention is the first to utilize simultaneous co-infection of producer cells with at least two different rHSV vectors to achieve production of rAAV. An unexpectedly high yield of rAAV was achieved through the use of simultaneous infection of producer cells with the rHSVs, as opposed to adding the two rHSVs at different times. The effect of timing of rHSV infection on rAAV yields showed that deviation from the simultaneous co-infection protocol was markedly detrimental to the rAAV yield. For example, introduction of a delay of merely 4 hours between infection with the first and second rHSV resulted in reduction to about 35% of the level of rAAV produced by simultaneous co-infection. With delays of 12 and 24 hours, production of rAAV dropped to insignificant levels.

Another factor in maximizing rAAV production is the ratio of the two rHSV viruses used in the simultaneous co-infection procedure. In a particular embodiment of the invention in which the first rHSV was rHSV/rc and the second rHSV was rHSV/AAV-GFP, best results were obtained when the ratio of the first rHSV to the second rHSV was about 8:1. This ratio is likely to differ with other rHSV used in the invention, and may be determined experimentally with each combination of first and second rHSV selected for use.

Methods of the invention described herein utilize simultaneous co-infection with at least two rHSVs to deliver the minimal set of components required to produce rAAV to the producer cells. Those of skill in the art will recognize that the disclosed simultaneous co-infection method can be modified to include further steps designed to deliver other components to the cells. Examples of such further steps include, but are not limited to, e.g., infection with at least one other virus, including 1) other rHSV differing in construction from the first and second rHSV, or 2) other strains of naturally occurring or recombinant viruses such as Ad, rAAV, Ad, or recombinant Ad (rAd). Infection with the additional virus can be either simultaneous with the co-infection with the first and second rHSV, or may be carried out either before or after the simultaneous co-infection with the first and second rHSV. Alternatively, or in addition to, the step of infection with at least one additional virus, the method can include an additional step involving transfection with at least one plasmid DNA, including an AAV expression vector, so long as a simultaneous co-infection step is performed.

In another aspect, the invention includes a population of producer cells containing at least 6000 infectious rAAV per cell. Such a population can be produced according to the disclosed methods. A preferred cell line is 293, but production of populations of producer cells can be achieved using any other cell line suitable for the purpose. Examples of other suitable human or monkey cell lines include Vero, WI 38 and HeLa.

The invention also encompasses a kit for production of high titer rAAV including a first rHSV containing rep and cap genes, a second rHSV including AAV ITRs and a promoter, and instructions for use. Any combination of the first and second rHSV as described above can be included in the kit. Inclusion of additional viruses or plasmids for use with the first and second rHSV are also within the scope of the kit. In some embodiments, the kit may further include a producer cell line and a cell line for titration of the rAAV.

The gain in efficiency of rAAV yield per cell achievable using the disclosed methods and compositions of the invention will be particularly advantageous for the commercial production of rAAV. By providing the benefit of at least ten-fold reduction in the requirements for cell culture, the invention offers the potential for significant savings in facilities producing rAAV on the scale needed for therapeutic use in gene therapy.

3.0 BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1 is a graph of comparative rAAV production data using simultaneous co-infection and single infection protocols.

Figure 2:
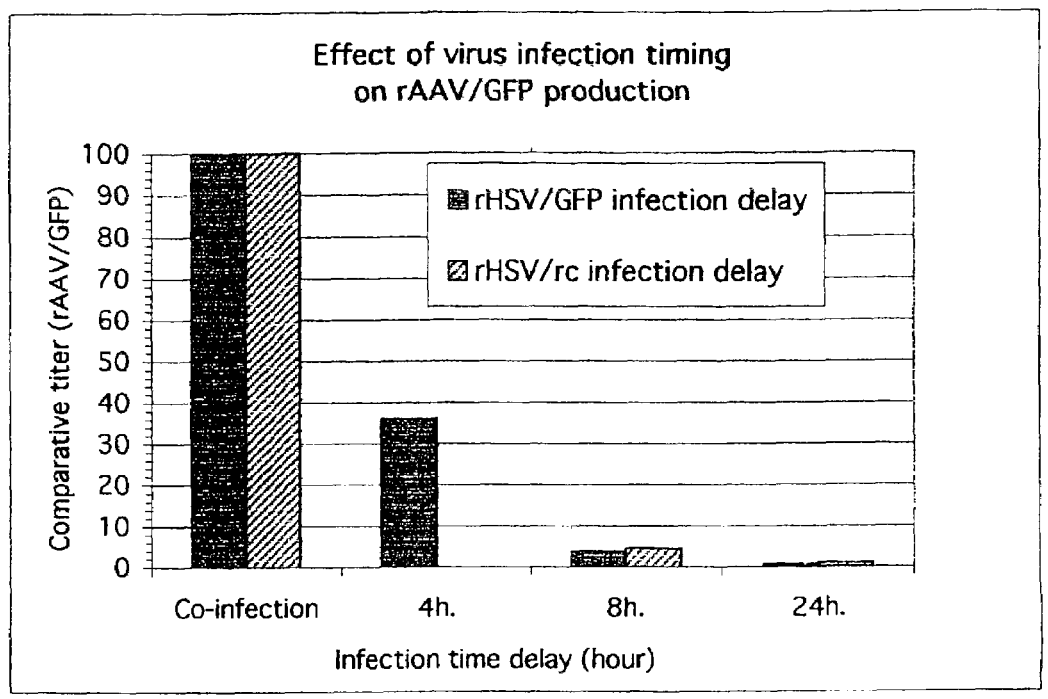

FIG. 2. Effect on rAAV production of varying the timing of addition of rHSV/rc and rHSV/GFP to the producer cells.

Figure 3:
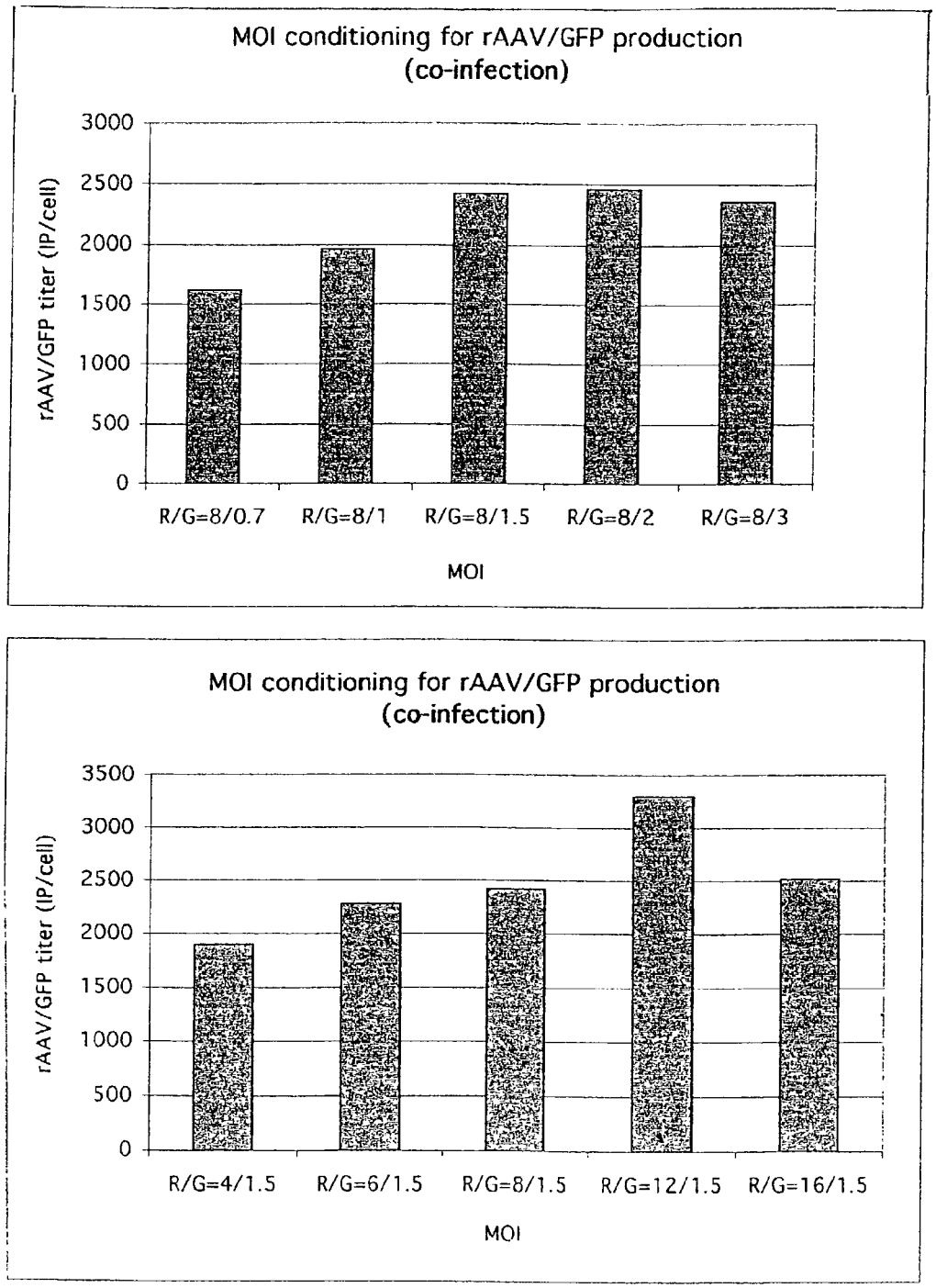

FIG. 3. Two graphs showing effect on rAAV production of varying the proportion of rHSV/rc (R) and rHSV/GFP (G) in the co-infection protocol.

Figure 4:
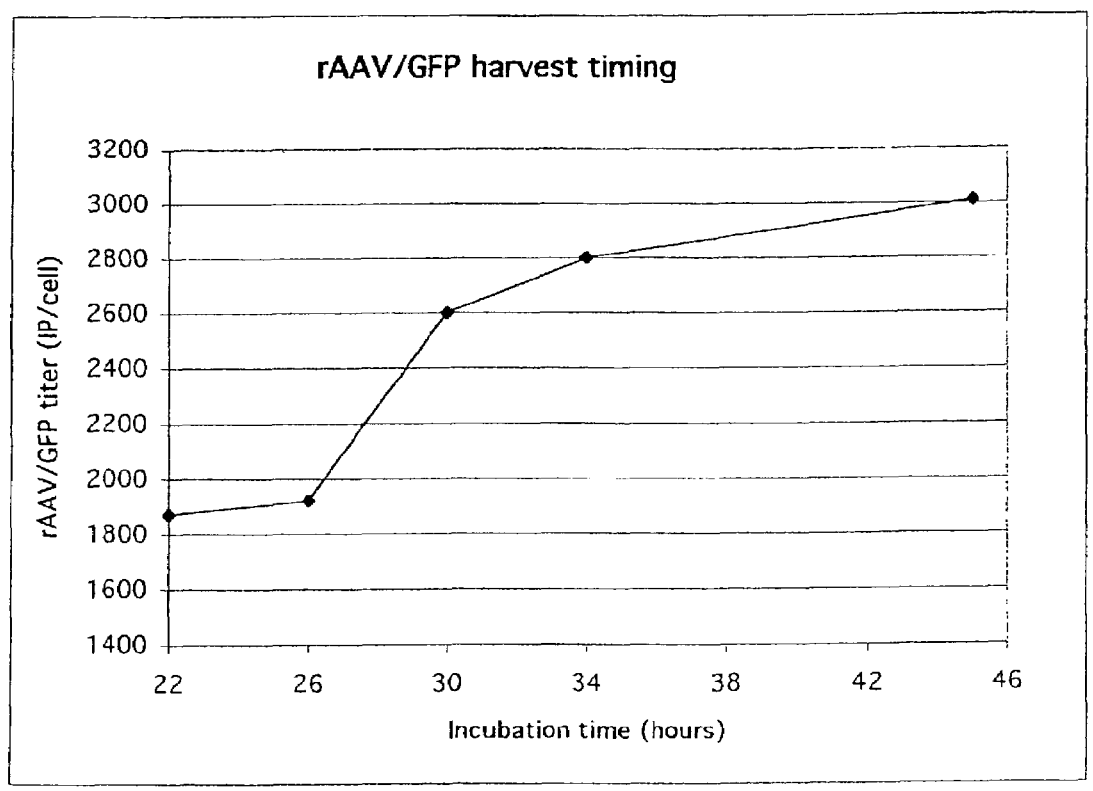

FIG. 4. Effect on rAAV production of varying the timing of harvest of the producer cells.

Figure 5:
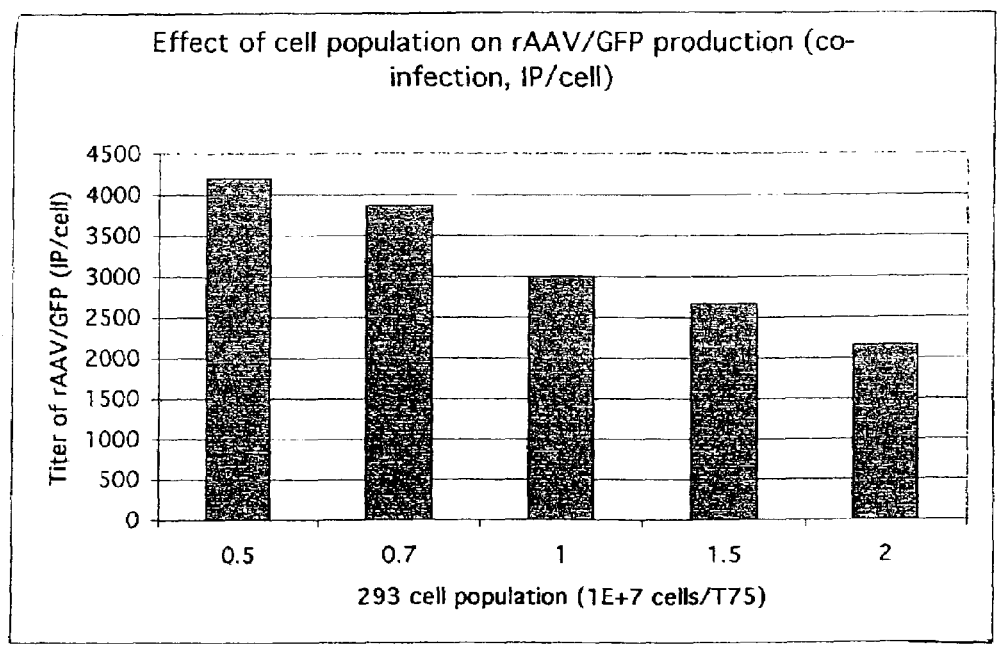

FIG. 5. Effect of seeding density of producer cells (293) on production of rAAV.

Figure 6:
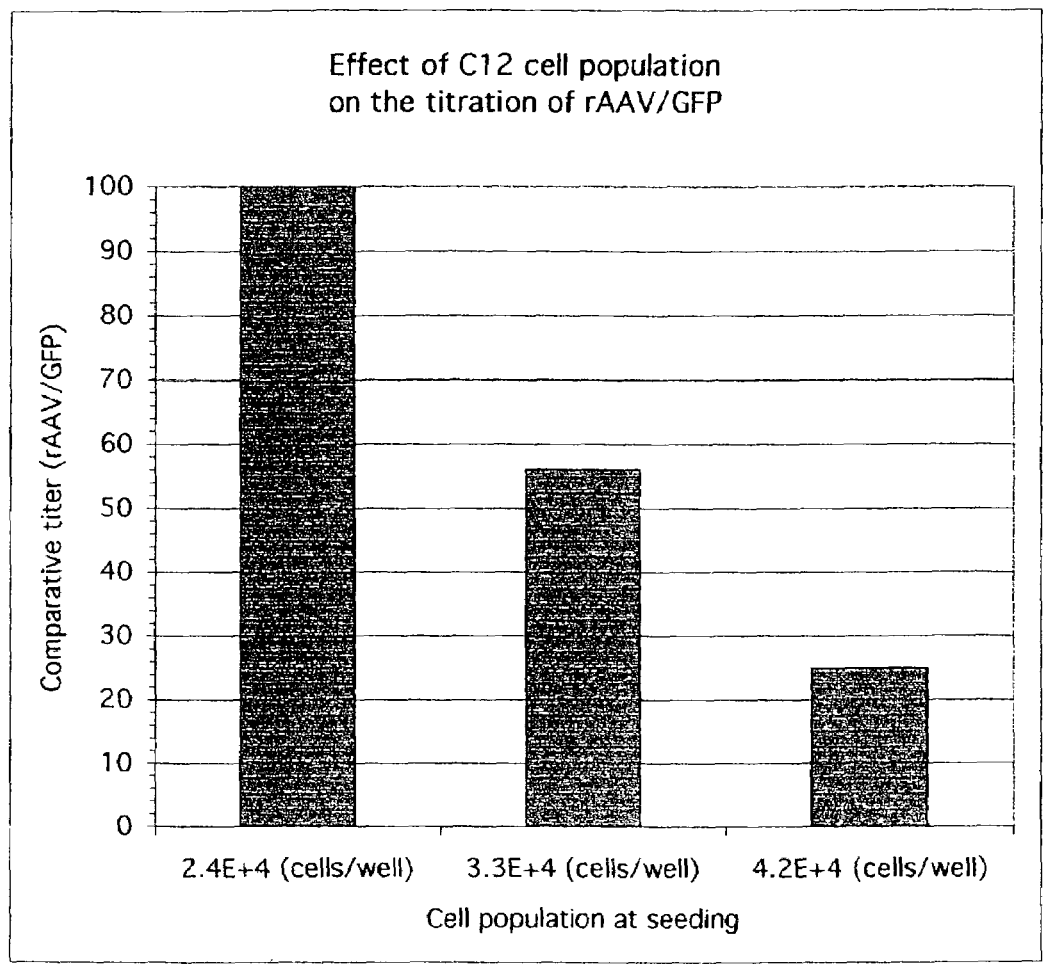

FIG. 6. Effect of seeding density of C12 cells on quantitation of rAAV/GFP.

Figure 7:
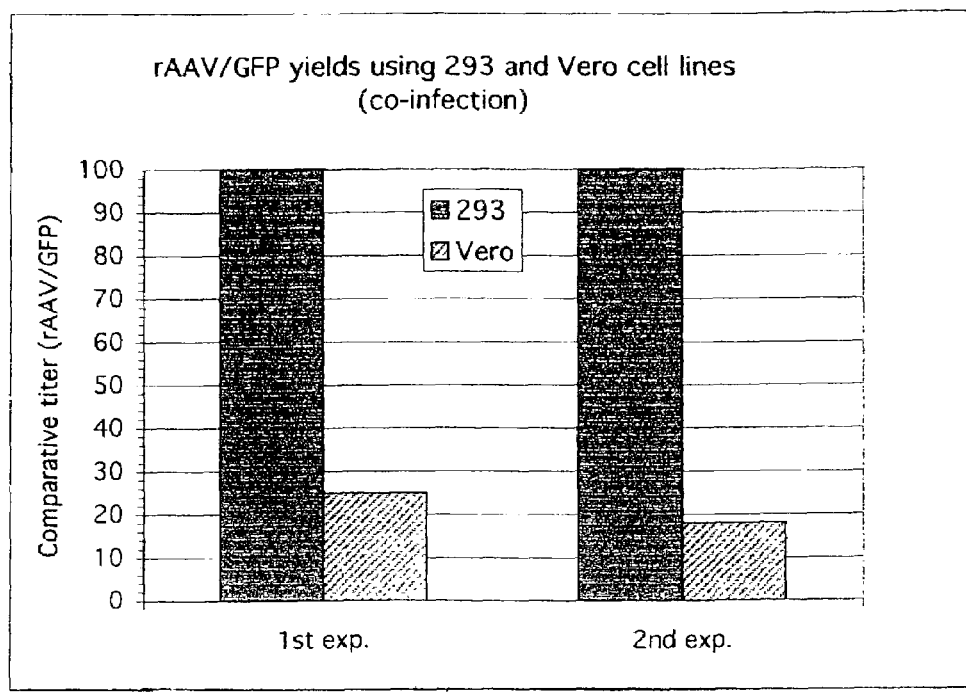

FIG. 7. Comparison of rAAV /GFP yields using 293 and Vero as producer cells.

4.0 DETAILED DESCRIPTION 4.1 Definitions

As used herein, the term "infection" refers to delivery of heterologous DNA into a cell by a virus. The term "simultaneous co-infection" denotes simultaneous infection of a producer cell with at least two viruses. The meaning of the term "co-infection" as used herein means "double infection," "multiple infection," or "serial infection" but is not used to denote simultaneous infection with two or more viruses. Infection of a producer cell with two (or more) viruses at different times will be referred to as "co-infection." The term "transfection" refers to a process of delivering heterologous DNA to a cell by physical or chemical methods, such as plasmid DNA, which is transferred into the cell by means of electroporation, calcium phosphate precipitation, or other methods well known in the art.

As used herein, the term "transgene" refers to a heterologous gene, or recombinant construct of multiple genes ("gene cassette") in a vector, which is transduced into a cell. Use of the term "transgene" encompasses both introduction of the gene or gene cassette for purposes of correcting a gene defect in the cell for purposes of gene therapy, and introduction of the gene or gene cassette into a producer cell for purposes of enabling the cell to produce rAAV. By the term "vector" is meant a recombinant plasmid or viral construct used as a vehicle for introduction of transgenes into cells.

The terms "recombinant HSV," "rHSV," and "rHSV vector" refer to isolated, genetically modified forms of herpes simplex virus (HSV) containing heterologous genes incorporated into the viral genome. By the term "rHSV/rc" or "rHSV/rc virus" is meant a rHSV in which the AAV rep and cap genes have been incorporated into the rHSV genome. The terms "rHSV expression virus," and "rHSV/AAV" denote a rHSV in which inverted terminal repeat (ITR) sequences from AAV have been incorporated into the rHSV genome. The terms "rHSV/AAV-GFP" and "rHSV/GFP" refer to an rHSV/AAV in which the DNA sequence encoding green fluorescent protein (GFP) has been incorporated into the viral genome.

The term "producer cell" refers to cell lines used for production of rAAV, into which heterologous genes are typically introduced by viral infection or transfection with plasmid DNA.

The term "AAV-GFP" refers to an infectious recombinant AAV particle containing a heterologous gene, i.e., GFP.

4.2 Gene Therapy Using rAAV Vectors

The invention provides a novel method of producing recombinant adeno-associated virus (rAAV). Recent efforts to use rAAV as a vehicle for gene therapy hold promise for its applicability as a treatment for human diseases based on genetic defects. The ability of rAAV vectors to integrate into the chromosomes of host cells makes it possible for rAAV to mediate long-term, high level expression of the introduced genes. An additional advantage of rAAV is its ability to perform this function in non-dividing cell types including hepatocytes, neurons and skeletal myocytes. rAAV has been used successfully as a gene therapy vehicle to enable expression of erythropoietin in skeletal muscle of mice (Kessler et al., 1996), tyrosine hydroxylase and aromatic amino acid decarboxylase in the CNS in monkey models of Parkinson disease (Kaplitt et al., 1994) and Factor IX in skeletal muscle and liver in animal models of hemophilia. At the clinical level, the rAAV vector has been used in human clinical trials to deliver the cftr gene to cystic fibrosis patients and the Factor IX gene to hemophilia patients (Flotte, et al., 1998, Wagner et al, 1998).

4.3 Required Elements of rAAV Production Systems

Recombinant AAV is produced in vitro by introduction of gene constructs into cells known as producer cells. Known systems for production of rAAV employ three fundamental elements: 1) a gene cassette containing the gene of interest, 2) a gene cassette containing AAV rep and cap genes and 3) a source of "helper" virus proteins.

The first gene cassette is constructed with the gene of interest flanked by inverted terminal repeats (ITRs) from AAV. ITRs function to direct integration of the gene of interest into the host cell genome. (Hermonat and Muzyczka, 1984, Samulski, et al., 1983). The second gene cassette contains rep and cap, AAV genes encoding proteins needed for replication and packaging of rAAV. The rep gene encodes four proteins (Rep 78, 68, 52 and 40) required for DNA replication. The cap genes encode three structural proteins (VP1, VP2, and VP3) that make up the virus capsid (Muzyczka and Berns, 2001.)

The third element is required because AAV-2 does not replicate on its own. Helper functions are protein products from helper DNA viruses that create a cellular environment conducive to efficient replication and packaging of rAAV. Adenovirus (Ad) has been used almost exclusively to provide helper functions for rAAV. The gene products provided by Ad are encoded by the genes E1a, E1b, E2a, E4orf6, and Va (Samulski et al., 1998; Hauswirth et al., 2000; Muzyczka and Burns, 2001.)

4.4 Production Technologies for rAAV

Production of rAAV vectors for gene therapy is carried out in vitro, using suitable producer cell lines such as 293 and HeLa. A well known strategy for delivering all of the required elements for rAAV production utilizes two plasmids and a helper virus. This method relies on transfection of the producer cells with plasmids containing gene cassettes encoding the necessary gene products, as well as infection of the cells with Ad to provide the helper functions. This system employs plasmids with two different gene cassettes. The first is a proviral plasmid encoding the recombinant DNA to be packaged as rAAV. The second is a plasmid encoding the rep and cap genes. To introduce these various elements into the cells, the cells are infected with Ad as well as transfected with the two plasmids. Alternatively, in more recent protocols, the Ad infection step can be replaced by transfection with an adenovirus "helper plasmid" containing the VA, E2A and E4 genes (Xiao, et al., 1998, Matsushita, et al., 1998).

While Ad has been used conventionally as the helper virus for rAAV production, it is known that other DNA viruses, such as Herpes simplex virus type 1 (HSV-1) can be used as well. The minimal set of HSV-1 genes required for AAV-2 replication and packaging has been identified, and includes the early genes UL5, UL8, UL52 and UL29 (Muzyczka and Burns, 2001). These genes encode components of the HSV-1 core replication machinery, i.e. the helicase, primase, primase accessory proteins, and the single-stranded DNA binding protein (Knipe, 1989; Weller, 1991). This rAAV helper property of HSV-1 has been utilized in the design and construction of a recombinant Herpes virus vector capable of providing helper virus gene products needed for rAAV production (Conway et al., 1999).

4.5 Quantitative Limitations of Current rAAV Production Techniques

Efficient, large scale production of rAAV will be necessary in order for gene therapy to become a practical treatment for human disease. It is estimated that for clinical effectiveness, over $10^{14}$ particles per dose of rAAV will be necessary for most applications (Snyder, et al., 1997, Ye et al., 1999). Conventional rAAV techniques involving plasmid transfection are capable of producing approximately 500 rAAV particles per cell (Conway et al., 1997).

The most advanced production systems for rAAV, including Ad-free transfection based methods, rep and cap inducible cell lines, and the use of recombinant adenovirus or recombinant Herpes virus are reported to produce approximately $5 \times 10^4$ particles of rAAV per cell (Conway et al., 1999, Xiao, et al., 1998, Matsushita, et al., 1998, Gao et al., 1998). To determine the number of infective particles per cell, this number must be reduced by about one hundred fold. The actual number of infectious particles per cell is typically about two orders of magnitude lower than the total number of particles per cell, assuming a typical particle to infectivity ratio of 100:1. Therefore even the most advanced production techniques typically produce about 500 infectious particles per cell. Using any of the rAAV production protocols currently known, at least $2 \times 10^9$ cells would have to be infected or transfected to produce $10^{14}$ particles of rAAV. Therefore to produce enough infectious rAAV for even one dose using current methodology, it would be necessary to culture over $2 \times 10^{11}$ cells (approximately 6500 tissue culture flasks). This level of cell culture surpasses what realistically can be accomplished using standard laboratory tissue culture methods, and is the most serious practical barrier to large scale commercial production of rAAV.

4.6 Recombinant Herpes Virus-based Simultaneous Co-infection Protocol for rAAV Production: An Overview.

The invention provides a novel Ad-free, transfection-free method of making rAAV, based on the use of two or more recombinant rHSV-1 viruses used to simultaneously co-infect producer cells with all of the components necessary for rAAV production. It is possible to use HSV-1, an alternate DNA helper virus of AAV, in lieu of Ad to provide the helper functions needed for rAAV production. Like Ad, HSV-1 is able to fully support AAV replication and packaging (Knipe, 1989, Knipe, 1989, Buller, 1981, Mishra and Rose, 1990, Weindler et al., 1991, Johnson et al., 1997). The minimal set of HSV-1 genes required to replicate and package AAV is UL5, UL8, UL52 and UL29 (Weindler et al., 1991). These genes encode components of the HSV-1 core replication machinery and by themselves form nuclear prereplication centers that develop into mature replication foci (Weindler et al., 1991, Knipe, D. M. 1989). In the present invention, recombinant HSV-1 viruses are used to supply the helper functions needed for rAAV production.

The disclosed methods employ simultaneous use of at least two different forms of rHSV, each containing a different gene cassette. In addition to supplying the necessary helper functions, each of these rHSV viruses is engineered to deliver different AAV (and other) genes to the producer cells upon infection. The two rHSV forms used in the invention are referred to as the "rHSV/rc virus" and the "rHSV expression virus." The two are designed to perform different, yet complementary functions resulting in production of rAAV.

The rHSV/rc virus contains a gene cassette in which the rep and cap genes from AAV are inserted into the HSV genome. The rep genes are responsible for replication and packaging of the rAAV genome in host cells infected with AAV. The cap genes encode proteins that comprise the capsid of the rAAV produced by the infected cells. The rHSV/rc virus is used therefore to enable the producer cells to make the protein products of the AAV rep and cap genes.

The second recombinant HSV used in the invention is an "rHSV expression virus." A usual element of an rAAV production system is an expression cassette (or "expression vector") containing transgene DNA sequences encoding a gene(s) of interest, along with promoter elements necessary for expression of the gene. Expression vectors engineered for rAAV production are generally constructed with the gene of interest inserted between two AAV-2 inverted terminal repeats (ITRs). The ITRs are responsible for the ability of native AAV to insert its DNA into the genome of host cells upon infection or otherwise persist in the infected cells.

In conventional methods, the expression cassette (containing the AAV ITRs, a gene of interest and a promoter) is delivered to the producer cells by way of transfection with plasmid DNA including such constructs. Alternatively, the expression cassette is integrated into the genome of a specialized producer cell line, such as e.g. the 293-GFP. In the latter case, only helper functions need to be added to the producer cells in order to rescue the foreign DNA from the host cell genome, making it available for packaging into rAAV particles containing the recombinant DNA.

In contrast to these approaches, in the methods of the present invention, the expression cassette is incorporated into a second rHSV-1 virus, i.e. the rHSV expression virus described above. This second rHSV virus is used for simultaneous co-infection of the cells along with the rHSV-1/rc virus. In a particular embodiment of the rHSV expression virus useful as a marker of gene expression and described in the examples below, the expression cassette contained green fluorescent protein (GFP) as the gene of interest, driven by a CMV promotor. This embodiment of the rHSV expression virus is herein referred to as "rHSV/AAV/GFP," or simply "rHSV/GFP." The advantage of the strategy of using two or more rHSV viruses, is that both the need for transfection and the need for a specialized producer cell line are eliminated.

4.7 High Titer Production of rAAV Using rHSV-based Simultaneous Co-infection Protocols The invention provides a novel rHSV-based method for production of high titer rAAV. Following simultaneous co-infection of producer cells with two rHSV viruses, all of the components required for production of infectious rAAV particles are delivered to the cells without the need for transfection, a step known to reduce efficiency of rAAV production. Additionally, use of rHSV for provision of helper functions obviates the requirement for Ad, a helper virus conventionally used for this purpose. Thus two significant problems associated with previous rAAV production protocols are eliminated by the disclosed method.

Production levels of rAAV of up to at lest 5000–6000 i.p./cell were achieved using this method. In the development of the present invention, the production of rAAV was investigated using the simultaneous co-infection protocol of the invention. In some assays, the experimental design involved a comparison of the level of rAAV produced by two methods—1) the simultaneous co-infection method and 2) a method involving single infection with rHSV/rc. In a typical assay of this type, replicate cultures of unmodified producer cells (e.g. 293) were simultaneously co-infected with rHSV/rc and an rHSV expression virus (rHSV/GFP), whereas replicate cultures of 293-GFP (having AAV-GFP integrated into the cellular genome) were singly infected with only rHSV/rc.

Under identical experimental conditions, results consistently demonstrated that the simultaneous co-infection method was at least twice as effective as the single infection method. The numbers of infectious rAAV produced per cell by the simultaneous co-infection protocol ranged from about 2300–6000 i.p./cell. In contrast, under the same conditions, the range following single infection was from about 1200–1600 i.p./cell.

These production figures exceed those commonly obtained using even the most advanced production methods (Clark, 2002). For example, previous use of d27.1-rc, which is comparable to the rHSV/rc of the invention, resulted in 380 expression units (EU) of AAV-GFP produced from 293 cells following transfection with AAV-GFP plasmid DNA, and up to 480 EU/cell when the producer cell was GFP-92, a proviral 293-derived cell line (Conway et al., 1999). Results obtained using the method of the invention were an order of magnitude greater than this.

Studies described herein revealed that a number of experimental variables affected the production of rAAV using the simultaneous co-infection method. Of particular note was the observation that simultaneous co-infection with the two viruses, i.e. rHSV/rc and the rHSV expression virus was far superior to double or multiple infection with the same viruses. (i.e. infection with the first rHSV, followed by infection with the second rHSV after an interval of hours, e.g. 4–24). These experiments revealed the importance of the timing of the addition of the two viruses, demonstrating the clear superiority of co-infection over double infection, even with delays of as little as 4 hours between addition of the first and the second rHSV.

The relative amounts of the first and second viruses added at the time of simultaneous co-infection also had a pronounced effect on rAAV production. Best results were obtained when the ratio of a first virus (rHSV/rc) to a second virus (rHSV/GFP) was about 8:1.

Another parameter that significantly affects yields of rAAV in the co-infection protocol is the choice of cell line used for production of rAAV. Experiments designed to test two cell lines commonly used for rAAV production, i.e. 293 and Vero cells, demonstrated that of the two, 293 was clearly the cell line of choice, producing about 5 times the amount of rAAV as Vero cells grown, infected and harvested under the same conditions. Other variables that significantly affect yields of rAAV include the initial plating density of the producer cell line (e.g., 293) and the time of harvest of the producer cells.

4.8 Construction of Recombinant HSV-1 Viruses

The invention utilizes two or more rHSV viruses in a simultaneous co-infection protocol to produce rAAV. Methods of making rHSV from HSV-1 are known in the art (Conway et al., 1999).

rHSV/rc. In one embodiment of the invention, a recombinant HSV designated rHSV/rc was used to demonstrate the efficacy of the novel rAAV production method. This virus was based on a recombinant vector expressing the AAV-2 rep and cap genes in a mutant HSV-1 vector designated d27.1 (Rice and Knipe, 1990) and was prepared as previously described (Conway et al., 1999). As a result of the mutation, this vector does not produce ICP27. An advantage in the use of an ICP27 mutant for rAAV production is that host cell splicing of messenger RNA is known to be inhibited by ICP27 (Sandri-Goldin and Mendoza, 1992). ICP27 probably also effects the appropriate splicing of the AAV-2 rep and cap messages. This vector was chosen because it is replication defective and was expected to show reduced cytotoxicity compared with wild type (wt) HSV-1. in a non-permissive cell line.

The virus d27. 1 displays several other features that make its use advantageous for the design of a helper virus for rAAV production. First, it expresses the early genes known to be required for rAAV production (Weindler et al., 1991, Rice and Knipe, 1990). In addition, d27.1 over-expresses ICP8, the single-stranded DNA binding protein that is the product of UL29, one of the HSV-1 genes essential for AAV replication and packaging (Weindler et al., 1991, Rice and Knipe, 1990, McCarthy, et al., 1989). Increased expression of ICP8 would therefore be predicted to augment rAAV production. In one embodiment of the HSV/rc vector used in the invention, the AAV-2 rep and cap genes were expressed under control of their native promoters. The p5 and p19 promoters of AAV-2 control expression of Rep 78 and 68 and Rep 52 and 40, respectively. The p40 promoter controls expression of VP1, VP2 and VP3. It will be apparent to those of skill in the art that any other promotor suitable for the purpose can be used and is also within the scope of the invention. Examples of other suitable promoters include SV40 early promoter, and Herpes tk promoter, metallothianine inducible promoter, mouse mammary tumor virus promoter and chicken β-actin promotrr.

rHSV expression virus. The rHSV-1 expression virus of the invention was produced in much the same manner as rHSV/rc, by homologous recombination into the HSV-1 tk gene, starting with plasmids pHSV-106 and plasmid pTR-UF5. The latter is an AAV proviral construct with AAV-2 ITRs flanking both an eGFP and a neomycin resistance gene (neo) expression cassette, in which expression of the GFP is driven by the human CMV promotor (Conway et al., 1999). rHSV/GFP contains a CMV driven gfp expression cassette inside the AAV ITRs and was recombined into the tk locus of the virus d27.1-lacz.

4.9 rHSV Viruses Based on AAV Capsids from AAV-1, AAV-3 or AAV-4 Serotypes.

The invention includes a method for producing rAAV particles with capsid proteins expressed in multiple serotypes of AAV. This is achieved by co-infection of producer cells with a rHSV expression virus and with a rHSV/rc helper virus in which the cap gene products are derived from serotypes of AAV other than, or in addition to AAV-2. Recombinant AAV vectors have generally been based on AAV-2 capsids. It has recently been demonstrated that rAAV vectors based on capsids from AAV-1, AAV-3, or AAV-4 serotypes differ substantially from AAV-2 in their tropism Capsids from other AAV serotypes offer advantages in certain in vivo applications over rAAV vectors based on the AAV-2 capsid. First, the appropriate use of rAAV vectors with particular serotypes may increase the efficiency of gene delivery in vivo to certain target cells that are poorly infected, or not infected at all, by AAV-2 based vectors. Secondly, it may be advantageous to use rAAV vectors based on other AAV serotypes if re-administration of rAAV vector becomes clinically necessary. It has been demonstrated that re-administration of the same rAAV vector with the same capsid can be ineffective, possibly due to the generation of neutralizing antibodies generated to the vector (Xiao, et al., 1999, Halbert, et al., 1997). This problem may be avoided by administration of a rAAV particle whose capsid is composed of proteins from a different AAV serotype, not affected by the presence of a neutralizing antibody to the first rAAV vector (Xiao, et al., 1999). For the above reasons, recombinant AAV vectors constructed using cap genes from serotypes other than, or in addition to AAV-2 are desirable.

It will be recognized that the construction of recombinant HSV vectors similar to rHSV/rc but encoding the cap genes from other AAV serotypes (e.g. AAV-1, AAV-3 to AAV-8) is achievable using the methods described herein to produce rHSV/rc. The significant advantages of construction of these additional rHSV vectors are ease and savings of time, compared with alternative methods used for the large-scale production of rAAV. In particular, the difficult process of constructing new rep and cap inducible cell lines for each different capsid serotypes is avoided.

5.0 EXAMPLES

The invention is further described in the following examples, which do not limit the scope of the invention described in the claims.

5.1 Example 1

Materials and Methods

Recombinant HSV viruses. A recombinant HSV-1 helper virus, designated rHSV/rc, containing AAV-2 rep and cap genes, was constructed by homologous recombination techniques as previously described for a rHSV-1 vector designated d27.1-rc, (Conway et al., 1999). A second rHSV-1, a rHSV expression virus designated rHSV/GFP, containing the AAV-2 ITRs flanking GFP, was constructed as follows.

Cell Lines For rAAV Production And Titering. Vero, 293 and C12 cell lines were obtained from American Type Culture Collection (Rockville, Md.) Cell lines used for production of rAAV by infection with rHSV, defined herein as "producer cells," included 293, 293-GFP and in some cases Vero. The 293-GFP cell line is a 293-derived cell line, produced from plasmid pTR-UF5, in which the AAV-2 ITRs and GFP, driven by a CMV promotor, have been integrated into the genome of the cells (Conway et al., 1997).

Choice Of Producer Cells For rHSV Single And Co-infection Protocols. In many of the examples described herein involving production of rAAV by producer cells, the simultaneous co-infection technique using two rHSV to deliver all of the components required for rAAV production was compared with a single infection technique using only rHSV/rc. In the single infection protocol, the infections were carried out using the 293-GFP cell line, in which the protein of interest (GFP) is already present within the genetic makeup of the cells. Thus the producer cells for the single infection protocol were 293-GFP, whereas for the double infection protocols, the producer cells were unmodified 293 cells, complemented by supplying the GFP expression cassette in the second rHSV, i.e. rHSV/GFP. For both single and double infection protocols, the cell lines (either 293 or 293-GFP or Vero) were plated at the same density (generally $1 \times 10^7$ cells per T75 flask) and otherwise treated the same. In experiments designed to test the effect of varying 293 plating density, cells were seeded at initial plating densities of 0.5, 0.7, 1.0, 1.5 and $2.0 \times 10^7$ cells/flask.

Infection of Producer Cells With rHSV and Recovery of rAAV. Viruses used in the infection procedures were diluted from stock preparations to desired concentrations in DMEM, then added to the flasks containing 293 or 293-GFP or Vero producer cells. At the time of addition of the viruses, which was generally on the next day after plating, the cells were approximately 70–80% confluent. Titers of stock preparations of rHSV/rc and rHSV/GFP were in the range of $5 \times 10^7 - 1 \times 10^8$ infectious particles (IP)/ml. In some of the double infection protocols, varying proportions of rHSV/rc to rHSV/GFP were added, with the MOI of the two recombinant viruses ranging as follows: rc/GFP: 8/0.7, 8/1, 8/1.5, 8/2, 8/3, 4/1.5, 6/1.5, 12/1.5, and 16/1.5. In other experiments using the double infection protocol, optimal timing of addition of the two viruses was tested. In these experiments, rHSV/rc and rHSV/GFP were added to the 293 cells at different intervals rather than simultaneously. In a typical experiment, the two viruses were added to the cells either simultaneously, or with a delay of 4, 8 or 24 hours between the addition of the first and second virus. The effect of delaying the addition of either virus was tested, i.e. with either rHSV/rc or rHSV/GFP being added first.

Following an incubation interval, the virus-infected cells were harvested and pelleted. The cell pellet was then resuspended in 10 ml of DMEM and cell-associated rAAV was recovered from the producer cells by lysis of the cells using standard techniques involving three rounds of freezing and thawing (Conway et al., 1999). The cell lysates were then titrated for quantitation of infectious units of AAV-GFP. In experiments designed to test the optimal time of harvest, producer cells were harvested at various intervals (22, 26, 30, 34, 46 hours ) after infection.

Assay of Infectious rAAV. The C12 cell line is a HeLa-derived cell line with inducible AAV-2 rep gene expression (Clark et al., 1995). This cell line was employed in experiments used to assay the number of infectious rAAV particles produced by the production methods of the invention. For this purpose, C12 cells were generally seeded in 96-well plates at densities of $1.2-1.6 \times 10^4$ cells/ well. In some experiments designed to test the effect of C12 seeding density, a range of higher plating densities (2.4, 3.3, $4.2 \times 10^4$ cell/well) was used. The amount of AAV-GFP produced was determined using a fluorescent cell assay by titering the virus in the cell lysate by serial dilutions on C12 cells in 96 well plates after co-infection with adenovirus (MOI of 20) and counting fluorescent cells by fluorescence microscopy. The fluorescent assay used for this purpose has been previously described (Conway et al., 1999, Zolotukhin et al., 1999). The viral yield per cell was then calculated and the most efficient MOI was determined.

5.2 Example 2

Comparison of rAAV Production Levels Using Simultaneous Co-infection and Single Infection.

This example describes a novel adenovirus-free, transfection-free method of producing infectious rAAV particles using simultaneous co-infection of 293 cells with two recombinant HSV- 1 viruses, rHSV/rc and rHSV/GFP, and demonstrates the superiority of the new method over a single infection protocol using rHSV/rc alone in producer cells having an integrated AAV-GFP expression cassette inserted in the genome.

Assays were performed in which production of rAAV was compared using the single infection and co-infection protocols described in Example 1 above. FIG. 1 shows results from three separate experiments in which 293 or 293-GFP cells were plated concurrently at the same seeding density, and either singly infected with rHSV/rc (293-GFP cells) or co-infected with rHSV/rc and rHSV/GFP (293 cells). Following harvest and preparation of cell lysates containing rAAV-GFP produced by the two methods, C12 cells were infected with the rAAV-GFP and the numbers of infectious rAAV-GFP were determined. Results showed that under the identical conditions of the experiment, the simultaneous co-infection protocol was much more effective than single infection with only rHSV/rc. rAAV yields in the three experiments were 2300, 2600, and 2420 i.p./cell using the co-infection protocol, vs. 1600, 1400 and 1260, respectively for the single infection method. With the level of production using co-infection normalized to 100%, production using single infection was found to range from a low of about 52% to a high of about 65% of that obtained by co-infection (FIG. 1).

5.3 Example 3

Simultaneous Co-infection: Effect of Timing of Virus Infection

The above example demonstrates the superiority of a simultaneous co-infection protocol using two recombinant rHSV (rHSV/rc and rHSV/GFP) over single infection using only rHSV to deliver the rep and cap genes to the producer cells. This example, involving a co-infection protocol using rHSV/rc and rHSV/GFP, shows the effect of varying the time of infection with each of the recombinant viruses.

The experiments were carried out by either co-infection of replicate cultures of 293 cells with rHSV/rc and rHSV/GFP, or by double infection of the cells with one of the two viruses (at time 0) and addition of the other after an interval of 4, 8 or 24 hours. FIG. 2 shows results demonstrating that co-infection was markedly superior to multiple infection at each of the times indicated. With addition of rHSV/rc first, followed by rHSV/GFP after a delay of 4 hours, yield of rAAV dropped to about 30% of the value obtained by co-infection (590 vs. 1940 i.p./cell). With longer delays of 8 hours and 24 hours, production of rAAV was negligible (74 and 14 i.p./cell, respectively). Similar results were obtained when rHSV/GFP was added first, and rHSV/rc was added after a delay of 8 or 24 hours. In that case as well, production of rAAV was insignificant compared with the simultaneous co-infection values (86 and 20 i.p./cell, vs. 1940 i.p./cell) (FIG. 2).

5.4 Example 4

Simultaneous Co-infection: Effect of Varying rHSV Ratios

The previous example shows that co-infection is superior to multiple infection using two recombinant HSV viruses for production of rAAV in producer cells. This example, using simultaneous co-infection with rHSV/rc and rHSV/GFP, demonstrates the effect of varying the relative proportions of the two viruses in the co-infection procedure. All procedures were as described. For simplicity, the ratio of rHSV/rc to rHSV/GFP is abbreviated to "R/G."

FIG. 3 shows data from two experiments in which the R/G ratio was varied, in all cases with the value for R being higher than that for G. The values for the R/G ratio varied from a low of (8/0.7) to a high of (8/2). Results from this assay showed that best production occurred when the R/G ratio was 8:1, with a MOI of 12 and 1.5, respectively for R and G.

5.5 Example 5

Simultaneous Co-infection: Effect of Time of Harvest

This example demonstrates that the choice of timing for harvest of the producer cells can affect the yield of rAAV.

Assays were carried out as described, on replicate cultures of 293 cells co-infected under the same conditions with identical concentrations of R/G. Only the time of harvest was varied, from 22 to 46 hours after co-infection. Results of this assay (FIG. 4) reveal that highest yields of rAAV are obtained when the incubation period before harvest was 46 hours. When cell harvesting was performed between 22 and 26 hours after co-infection, the yield of rAAV-GFP was approximately 1900 infectious particles (i.p.) per cell. In contrast, delay of harvest to 26, 34 and 46 hours after co-infection resulted in improvements in yield of about 2600, 2800 and 3000 i.p./cell, respectively (FIG. 4).

5.6 Example 6

Simultaneous Co-infection: Effect of 293 Cell Seeding Density

To determine the effect of seeding density of the producer cells on rAAV-GFP production, 293 cells were plated at five seeding densities ranging from $0.5$–$2.0 \times 10^7$ cells per T75 flask. Following co-infection with rHSV/rc and rHSV/GFP, cells were harvested and rAAV production was quantitated. Results showed a progressive decline in production of rAAV at each of the seeding densities above $0.5 \times 10^7$ cells per flask (FIG. 5). In the experiments shown, production values for 0.5, 0.7, 1.0, 1.5 and $2.0 \times 10^7$ were 4200, 3860, 3000, 2660, and 2160 i.p./cell.

5.7 Example 7

Simultaneous Co-infection: Effect of C12 Cell Density

The number of infectious rAAV contained in the cell lysate from the producer cells was determined by infection of a second cell line with the rAAV. The cell line used for this purpose was C12. To determine the effect of seeding density of C12 cells for this assay, C12 cells were plated at various seeding densities and used for analysis of rAAV-GFP production following treatment with lysates from 293 producer cells co-infected with rHSV/rc and rHSV/GFP. The results, shown in FIG. 6, demonstrated that optimal sensitivity of the fluorescence assay was obtained from cells seeded at the lowest density, i.e. $2.4 \times 10^4$ cells/well. At higher initial plating densities, detection sensitivity was reduced to about 55% and 25%, respectively, for cells seeded at $3.3 \times 10^4$ and $4.2 \times 10^4$ cells/well.

5.8 Example 8

Simultaneous Co-infection: Comparison of Producer Cell Lines

This example shows a comparison of the effectiveness of 293 cells as compared with Vero cells for rAAV production. For these assays, 293 cells and Vero cells were treated identically. Results of two separate experiments are shown in FIG. 6, in which it is clearly demonstrated that 293 cells are superior to Vero cells for the production of rAAV using the above co-infection protocol using rHSV/rc and rHSV/GFP. In the first of the two experiments shown, the 293 cells produced 1940 i.p/cell whereas under the same conditions, Vero cells produced 480 i.p./cell. In the second experiment, the respective production levels were 4000 vs. 720 i.p./cell.

5.9 Example 9

Simultaneous Co-infection Using Alternate rHSV Vectors

The capsid proteins of a rAAV product are determined by the serotype of the AAV rep used in the construction of the rHSV/rc. The following example provides a method of producing rAAV with capsids based on various AAV serotypes, using the simultaneous co-infection protocol described above.

Construction of rHSV Viruses. Methods have been described for construction of rHSV vectors expressing the AAV-2 rep genes (Conway et al., 1999). The product of such a viral vector, used in conjunction with a rHSV expression virus, is a rAAV with AAV-2 serotype 2 capsid proteins. Alternate recombinant HSV vectors expressing the AAV-2 rep genes and either the AAV-1, AAV-3 or AAV-4 cap genes may be obtained as follows. AAV-1 through AAV-8 may be acquired from American Type Culture Collection. 293 cells are plated onto 60 mm dishes. 24 hours later, the 293 cells are infected with the desired AAV serotype (MOI of 500 particles per cell) and then co-infected with Ad (MOI of 10) to produce double-stranded replicative intermediates of the AAV genomes. Twenty four hours after infection, low molecular weight DNA is isolated by Hirt extraction as described by Conway et al., (1997). This DNA then serves as a template for PCR amplification of the AAV cap genes. PCR primers specific for the particular AAV serotype cap genes are used to amplify the cap gene from the appropriate template. These primers have KpnI sites incorporated at their 5' end. The PCR reaction conditions are standard conditions for denaturing, annealing, and extension that have previously been employed (Conway et al., 1997).

PCR products are separated by gel electrophoresis and purified. PCR products are then sequenced to verify the fidelity of the PCR reaction. The cap gene PCR products are then digested with KpnI. The vector pHSV-106-rc encodes the BamHI region of the HSV-1 tk locus into which the AAV-2 rep and cap genes have been cloned. The vector pHSV-106-rc is the integration vector used to construct d27.1-rc. pHSV-106-rc is also digested with KpnI to cut out the AAV-2 cap gene 3' of the p40 promoter. AAV cap genes from the serotype of interest are then cloned in frame into this KpnI site. This results in constructs (pHSV-106-rc1, pHSV-106-rc3, and pHSV-106-rc4) in which the entire VP-3 protein (which comprises 90% of the viral capsid) is from the new AAV serotype. The cloning site used for this purpose is downstream of the p40 promoter, ensuring that regulation of cap transcription by the AAV-2 p40 promoter and Rep proteins is not be altered.

To construct the recombinant viruses (e.g. d27.1-rc1, d27.1-rc3, d27.1-rc4, d27.1-rc5, d27.1-rc6, d27.1-rc7, d27.1-rc8) the constructs pHSV-106-rc1, pHSV-106-rc3, and pHSV -106-rc4 are linearized by restriction digest. Each virus is then separately cotransfected into V27 cells along with d27.1-lacz infected cell DNA. This procedure as well as isolation of recombinant clones by limiting dilution has been described in detail and was used to make the original virus, d27.1-rc. (Conway et al., 1999). Restriction digest of recombinant viral DNA and sequencing of the viral genome is used to verify integration of the vector into the HSV genome. The efficiency of the recombinants at producing rAAV is then determined as described for d27.1-rc.

Co-infection Protocols. The simultaneous co-infection protocols described are amenable to use with any rHSV/rc helper virus. While a rHSV/rc based on the capsid proteins of the AAV-2 serotype was used to demonstrate the invention, it is apparent that rHSV vectors based on other AAV serotypes may be employed Except for choice of AAV serotype (AAV-1, 2,3, 4, 5, 6, 7, 8, and other possible serotypes) in the rHSV/rc, all other steps in the procedure for production of rAAV would remain the same.

6.0 REFERENCES

Buller, R. M. L. 1981. Herpes simplex virus types 1 and 2 completely help adnovirus-associated virus replication. *J Virol* 40:241–247.

Chiorini, J. A., L. Yang, Y. Liu, B. Safer, and R. M. Kotin. 1997. Cloning of adeno-associated virus type 4 (AAV4) and generation of recombinant AAV4 particles. J Virol 71:6823–6833.

Chiorini, J. A., F. Kim, L. Yang, and R. M. Kotin. 1999. Cloning and characterization of adeno-associated virus type 5. J Virol 73:1309–1319.

Clark, K. R., F. Voulgaropoulou, D. M. Fraley, and P. R. Johnson. 1995. Cell lines for the production of recombinant adeno-associated virus. Hum Gene Ther 6:1329–1341.

Clark, K. R. 2002. Recent advances in recombinant adeno-associated virus vector production. Kidney Internat. 61, Symposium 1:S9–S15.

Conway, J. E., S. Zolotukhin, N. Muzyczka, G. S. Hayward, and B. J. Byrne. 1997. Recombinant adeno-associated virus type 2 replication and packaging is entirely supported by a herpes simplex virus type 1 amplicon expressing Rep and Cap. J Virol 71:8780–8789.

Conway, J. E., C. M. J. ap Rhys, I. Zolotukhin, S. Zolotukhin, N. Muzyczka, G. S. Hayward, and B. J. Byrne. 1999. High-titer recombinant adeno-associated virus production utilizing a recombinant herpes simplex virus type I vector expressing AAV-2 Rep and Cap. Gene Ther. 6:973–985.

Flotte, T. R. and B. J. Carter. 1998. Adeno-associated virus vectors for gene therapy of cystic fibrosis. Methods Enzymol 292:717–732.

Gao, G. P., G. Qu, L. Z. Faust, R. K. Engdahl, W. Xiao, J. V. Hughes, P. W. Zoltick, and J. M. Wilson. 1998. High-titer adeno-associated viral vectors from a Rep/Cap cell line and hybrid shuttle virus. Hum Gene Ther 9:2353–236

Halbert, C. L., T. A. Standaert, M. L. Aitken, I. E. Alexander, D. W. Russell, and A. D. Miller. 1997. Transduction by adeno-associated virus vectors in the rabbit airway: efficiency, persistence, and readministration. J Virol 71:5932–5941.

Hauswirth, W. W., A. S. Lewin, S. Zolotukhim and N. Muzyczcka. 2000. Production and purification of recombinant adeno-associated virus. Methods Enzymol. 316:743–761.

Hermonat, P. L. and N. Muzyczka. 1984. Use of adeno-associated virus as a mammalian DNA cloning vector: transduction of neomycin resistance into mammalian tissue culture cells. Proc Natl Acad Sci USA 81:6466–6470.

Herzog, R. W., J. N. Hagstrom, S. H. Kung, S. J. Tai, J. M. Wilson, K. J. Fisher, and K. A. High. 1997. Stable gene transfer and expression of human blood coagulation factor IX after intramuscular injection of recombinant adeno-associated virus. Proc Natl Acad Sci USA 94:5804–5809.

Johnston, K. M., D. Jacoby, P. A. Pechan, C. Fraefel, P. Borghesani, D. Schuback, R. J. Dunn, F. I. Smith, and X. O. Breakefield. 1997. HSV/AAV hybrid amplicon vectors extend transgene expression in human glioma cells. *Hum Gene Ther* 8:359–370.

Iwaki, G. J. Kurtzman, K. J. Fisher, P. Colosi, L. B. Couto, and K. A. High. 1998. Adeno-associated viral vector-mediated gene transfer of human blood coagulation factor IX into mouse liver. Blood 91:4600–4607.

Kaplitt, M. G., P. Leone, R. J. Samulski, X. Xiao, D. W. Pfaff, K. L. O'Malley, and M. J. During. 1994. Long-term gene expression and phenotypic correction using adeno-associated virus vectors in the mammalian brain. *Nat Genet* 8:148–154.

Kessler, P. D., G. M. Podsakoff, X. Chen, S. A. McQuiston, P. C. Colosi, L. A. Matelis, G. J. Kurtzman and B. J. Byrne, 1996. Gene delivery to skeletal muscle in sustained expression and systemic delivery of a therapeutic protein. Proc. Natl. Acad. Sci. 93:14082–14087.

Koeberl, D. D., I. E. Alexander, C. L. Halbert, D. W. Russell, and A. D. Miller. 1997. Persistent expression of human clotting factor IX from mouse liver after intravenous injection of adeno-associated virus vectors. Proc Natl Acad Sci U S A 94:1426–1431.

Knipe, D. M. 1989. The role of viral and cellular nuclear proteins in herpes simplex virus replication. Adv.Virus Res. 37:85–123:85–123.

Kurtzman, and B. J. Byrne. 1996. Gene delivery to skeletal muscle results in sustained expression and systemic delivery of a therapeutic protein. *Proc Natl Acad Sci USA* 93:14082–14087.

Matsushita, T., Elliger S., Elliger, C., G. dsakoff, L. llarreal, G. Kurtzman, Y. Iwaki, and P. Colosi. 1998. Adeno-associated virus vectors can be efficienty produced without helper virus. Gene Ther 5:938–945.

McCarthy, A. M., L. McMahan, and P. A. Schaffer. 1989. Herpes simplex virus type 1 ICP27 deletion mutants exhibit altered patterns of transcription and are DNA deficient. J.Virol. 63:18–27.

Mishra, L. and J. A. Rose. 1990. Adeno-associated virus DNA replication is induced by genes that are essential for HSV-1 DNA synthesis. *Virology* 179:632–639.

Muzczka, N. 1992. Use of adeno-associated virus as a general transduction vector for mammalian cells. Curr Top Microbiol Immunol 158:97–129.

Muzczka, N. and K. I. Berns, 2001. Parvoviridae: The viruses and their replication, pp. 2327–2360. In D. M. Knipe and P. M. Howley (ed.), Fields Virology, Fourth Edition, Lippincott Williams and Wilkins, New York.

Monahan, P. E., R. J. Samulski, J. Tazelaar, X. Xiao, T. C. Nichols, D. A. Bellinger, M. S. Read, and C. E. Walsh. 1998. Direct intramuscular injection with recombinant AAV vectors results in sustained expression in a dog model of hemophilia. Gene Ther 5:40–49.

Rice, S. A. and D. M. Knipe. 1990. Genetic evidence for two distinct transactivation functions of the herpes simplex virus alpha protein ICP27. J.Virol. 64:1704–1715.

Rose, J. A. and F. Koezot. 1972. Adenoviurs-associated virus multiplication VII. Helper requirement for viral deoxyribonucleic acid and ribonucleic acid systhesis. *J Virol* 10:1–8.

Rutledge, E. A., C. L. Halbert, and D. W. Russell. 1998. Infectious clones and vectors derived from adeno-associated virus (AAV) serotypes other than AAV type 2. J Virol 72:309–319.

Samulski, R. J., M. Sally and N. Muzyczka. 1998. Adeno-associated viral vectors. Cold Spring Harbor Laboratory Press, Cold Spring Harbor, N.Y.

Samulski, R. J., A. Srivastava, K. I. Berns, and N. Muzyczka. 1983. Rescue of adeno-associated virus from recombinant plasmids: gene correction within the terminal repeats of AAV. Cell 33:135–143.

Sandri-Goldin, R. M. and G. E. Mendoza. 1992. A herpesvirus regulatory protein appears to act post-transcriptionally by affecting mRNA processing. Genes Dev. 6:848–863.

Snyder, R. O., S. K. Spratt, C. Lagarde, D. Bohl, B. Kaspar, B. Sloan, L. K. Cohen, and 0. Danos. 1997. Efficient and stable adeno-associated virus-mediated transduction in the skeletal muscle of adult immunocompetent mice. Hum Gene Ther 8:1891–1900.

Wagner, J. A., T. Reynolds, M. L. Moran, R. B. Moss, J. J. Wine, T. R. Flotte, and P. Gardner. 1998. Efficient and persistent gene transfer of AAV-CFTR in maxillary sinus. Lancet 351:1702–1703.

Weindler, F. W. and R. Heilbronn. 1991. A subset of herpes simplex virus replication genes provides helper functions for productive adeno-associated virus replication. *J Virol* 65:2476–2483.

Weller, S. K. 1991. Genetic analysis of HSV-1 gene required for genome replication. In: Herpes Virus Transcription and Its Regulation. CRC Press, Boca Raton, pp. 105–136.

Xiao, X., J. Li, and R. J. Samulski. 1998. Production of high-titer recombinant adeno-associated virus vectors in the absence of helper adenovirus. J Virol 72:2224–2232.

Xiao, W., N. Chirmule, S. C. Berta, B. McCullough, G. Gao, and J. M. Wilson. 1999. Gene therapy vectors based on adeno-associated virus type 1. J Virol 73:3994–4003.

Ye, X., V. M. Rivera, P. Zoltick, F. J. Cerasoli, M. A. Schnell, G. Gao, J. V. Hughes, M. Gilman, and J. M. Wilson. 1999. Regulated delivery of therapeutic proteins after in vivo somatic cell gene transfer. Science 283:88–91.

Zolotukhin, S., B. J. Byrne, E. Mason, I. Zolotukhin, M. Potter, K. Chesnut, C. Summerford, R. J. Samulski, and N. Muzyczka. 1999. Recombinant adeno-associated virus purification using novel methods improves infectious titer and yield. Gene Ther 6:986–993.

What is claimed is:

1. A method for producing high titer recombinant Adeno-Associated Virus (rAAV) comprising:
    (a) simultaneously co-infecting a 293 cell with
        (i) a first replication defective recombinant herpes simplex virus (rHSV) comprising a nucleic acid encoding an AAV rep and an AAV cap gene each operably linked to a promoter; and
        (ii) a second replication defective rHSV comprising rAAV internal terminal repeat (ITR) nucleic acid segments encoding rAAV ITRs, a gene of interest, and a promoter operably linked to said gene of interest;
    (b) incubating the 293 cell; and
    (c) following incubation, collecting rAAV from the 293 cell of step (b) wherein the titer is up to 2160–4200 infectious particles per cell.

2. The method of claim 1 wherein the AAV cap gene has a serotype selected from the group consisting of AAV-1, AAV-2, AAV-3, AAV-4, AAV-5, AAV-6, AAV-7, and AAV-8.

3. The method of claim 2 wherein the AAV cap gene serotype is AAV-2.

4. The method of claim 1 wherein the rep and cap genes are integrated into the thymidine kinase (tk) gene locus of the first rHSV.

5. The method of claim 1 wherein the promoter for each of the rep and the cap gene in the first rHSV is a heterologous promoter selected from the group consisting of CMV promoter, SV40 early promoter, Herpes tk promoter, metallothionine inducible promoter, mouse mammary tumor virus promoter and chicken β-actin promoter.

6. The method of claim 5 wherein the heterologous promoter is CMV promoter or chicken β-actin promoter.

7. The method of claim 1 wherein the promoter in the second rHSV is CMV promoter.

8. The method of claim 1 wherein the second rHSV further comprises a second gene of interest.

9. The method of claim 1 wherein the gene of interest encodes a reporter molecule.

10. The method of claim 9 wherein the reporter molecule is selected from the group consisting of beta-galactosidase, neomycin phosphoro-transferase, chloramphenicol acetyl transferase, thymidine kinase, luciferase, beta-glucuronidase, xanthine-guanine phosphoribosyl transferase, aminoglycoside, hygromycin B, dihydrofolate reductase/methotrexate and green fluorescent protein.

11. The method of claim 1 further comprising co-infecting with a third recombinant virus selected from the group consisting of rHSV, rAAV, and recombinant Adenovirus (rAd).

12. The method of claim 11 wherein co-infecting with the third recombinant virus is simultaneous with co-infecting with a first replication defective recombinant herpes simplex virus (rHSV) comprising a nucleic acid encoding an AAV rep and an AAV cap gene each operably linked to a promoter and a second replication defective rHSV comprising rAAV internal terminal repeat (ITR) nucleic acid segments encoding AAV ITRs, a gene of interest, and a promoter operably linked to said gene.

13. The method of claim 1 or 11 further comprising transfecting with at least one plasmid DNA including an AAV expression vector.

14. The method of claim 1 wherein the ratio of the first rHSV to the second rHSV is 1:1 to 10:1.

15. The method of claim 1 wherein the ratio of the first rHSV to the second rHSV is 4:1 to 8:1.

16. The method of claim 1 wherein the ratio of the first rHSV to the second rHSV is 8:1.

17. The method of claim 1 wherein the titer of infectious rAAV is 4000 infectious particles per cell.

18. The method of claim 1, wherein the gene of interest is a therapeutic gene.

19. The method of claim 18 wherein the therapeutic gene is selected from the group consisting of α-antitrypsin, GAA, erythropoietin and PEDF.

20. The method of claim 1 wherein the first rHSV is a replication defective ICP27 defective HSV mutant selected from the group. consisting of HSV mutant d27.1-rc1, d27.1-rc3, d27.1-rc4, d27.1-rc5, d27.1-rc6. d26.1-rc7 and d27.1-rc8.

21. The method of claim 20 wherein the replication defective HSV mutant is d27.1-rc8, which overexpresses ICP8.

22. The method of claim 1 wherein the promoter for the rep and cap genes in the first rHSV is a homologous promoter selected from the group consisting of p40, p5 and p19.

23. The method of claim 1 wherein the promoter for the rep and cap genes in the first rHSV or the second replication defective rHSV is a heterologous promoter.

24. A kit for producing high titer recombinant adeno-associated virus (rAAV) in a 293 cell comprising:
(a) a replication defective recombinant herpes simplex virus (rHSV) comprising AAV rep and cap genes;
(b) a replication defective rHSV virus comprising adeno-associated virus internal terminal repeats (AAV ITRs) and a promoter comprised within an expression vector;
(c) a 293 cell for rAAV virion production; and
(d) instructions for use.

25. The kit of claim 24 further comprising a 293 cell line for titration of rAAV.

26. A method for producing high-titer recombinant adeno-associated virus (rAAV) comprising:
(a) infecting a 293 cell simultaneously or serially within about 4 hours with
 (i) a first replication defective recombinant herpes simplex virus (rHSV) comprising a nucleic acid encoding an AAV rep and an AAV cap gene each operably linked to a promoter; and
 (ii) a second replication defective rHSV comprising rAAV internal terminal repeat (ITR) nucleic acid segments encoding AAV ITRs, a gene of interest, and a promoter operably linked to said gene;
(b) incubating the 293 cell; and
(c) following incubation collecting rAAV from the 293 cell of step (b) cell.

* * * * *